United States Patent
Bannerjee et al.

(10) Patent No.: US 11,593,469 B2
(45) Date of Patent: Feb. 28, 2023

(54) CONTINUOUSLY VALIDATING A USER DURING AN ESTABLISHED AUTHENTICATED SESSION USING PHOTOPLETHYSMOGRAM AND ACCELEROMETER DATA

(71) Applicant: Tata Consultancy Services Limited, Mumbai (IN)

(72) Inventors: Tanushree Bannerjee, Kolkata (IN); Venkata Subramanian Viraraghavan, Bangalore (IN); Kartik Muralidharan, Bangalore (IN); Dibyanshu Jaiswal, Kolkata (IN); Mithun Basaralu Sheshachala, Bangalore (IN); Ramesh Kumar Ramakrishnan, Bangalore (IN); Arpan Pal, Kolkata (IN); Balamuralidhar Purushothaman, Bangalore (IN)

(73) Assignee: Tata Consultancy Services Limited, Mumbai (IN)

( * ) Notice: Subject to any disclaimer, the term of this patent is extended or adjusted under 35 U.S.C. 154(b) by 151 days.

(21) Appl. No.: 17/212,659

(22) Filed: Mar. 25, 2021

(65) Prior Publication Data
US 2021/0303668 A1    Sep. 30, 2021

(30) Foreign Application Priority Data
Mar. 30, 2020    (IN) .............................. 202021014033

(51) Int. Cl.
*G06F 21/32*    (2013.01)
*A61B 5/024*    (2006.01)
(Continued)

(52) U.S. Cl.
CPC .......... *G06F 21/32* (2013.01); *A61B 5/02427* (2013.01); *A61B 5/117* (2013.01);
(Continued)

(58) Field of Classification Search
CPC ..................... G06F 21/32; G06F 21/34; G06F 2221/2139; A61B 5/02427; A61B 5/117;
(Continued)

(56) References Cited

U.S. PATENT DOCUMENTS 9,693,711 B2    7/2017  Yuen et al.

FOREIGN PATENT DOCUMENTS

WO    WO2017132061 A1    8/2017

OTHER PUBLICATIONS

Decision to Grant a European Patent Pursuant to Article 97(1) EPC dated Jun. 23, 2022, for EP Patent Application No. 21 163 610.5; 2 pages.
Communication about intention to grant a European Patent received from the European Patent Office in EP Application No. 21 163 610.5, 6 pages, dated Feb. 2, 2022.
Extended European Search Report issued by the European Patent Office in counterpart European Patent Application No. 21 163 610.5, 2 pages, dated Aug. 4, 2021.
(Continued)

*Primary Examiner* — Mohammad W Reza
(74) *Attorney, Agent, or Firm* — Finnegan, Henderson, Farabow, Garrett & Dunner, LLP

(57) ABSTRACT

Embodiments herein provide a method and system for continuously validating a user during an established authenticated session using Photoplethysmogram (PPG) and accelerometer data. State of the art approaches are mostly based on feature extraction and ML modelling for PPG based continuous session validation, while a template based approach in the art follows a complicated approach. The method disclosed herein utilizes less computation intensive template based approach to continuously validate the user across the session. The method comprises preprocessing a PPG data or PPG signal acquired from a wearable device worn by the user to identify segments of negligible motion.
(Continued)

A first segment, after authentication using conventional authentication mechanism, serves as the initial reference. The chosen segments are then tested one by one with respect to the reference. If the templates in a segment match those of the reference, it is updated as the new reference, else a re-authentication is triggered.

15 Claims, 9 Drawing Sheets

(51) Int. Cl.
    *A61B 5/117*     (2016.01)
    *A61B 5/00*     (2006.01)
    *G06F 21/34*     (2013.01)

(52) U.S. Cl.
    CPC ............ *A61B 5/721* (2013.01); *A61B 5/7246* (2013.01); *G06F 21/34* (2013.01); *A61B 2562/0219* (2013.01); *G06F 2221/2139* (2013.01)

(58) Field of Classification Search
    CPC ............... A61B 5/721; A61B 5/7246; A61B 2562/0219; H04L 9/12; H04L 2209/805; H04L 9/0866; H04L 9/3231
    See application file for complete search history.

(56) References Cited

OTHER PUBLICATIONS

Transmission of Certificate for a European patent pursuant to Rule 74 EPC, issued Aug. 2, 2022, for EP Patent Application No. 21 163 610.5; 1 page.

Wu et al.; "A Continuous Identity Authentication Scheme Based on Physiological and Behavioral Characteristics", Sensors, vol. 18, No. 2, (2018).

Blasco et al.; "A Survey of Wearable Biometric Recognition Systems", ACM Computing Surveys, ACM, New York, NY, vol. 49, No. 3, pp. 1-35, (2016).

Ekiz, Deniz et al., "Is Your Smartband Smart Enough to Know Who You Are: Towards Continuous Physiological Authentication in The Wild", Computer Science, Dec. 2019, Arxiv, https://arxiv.org/pdf/1912.04760.pdf.

Li, Jingzhen et al., "An Approach to Biometric Verification Based on Human Body Communication in Wearable Devices", Sensors, Jan. 2017, vol. 17, MDPI, https://www.researchgate.net/publication/312207310_An_Approach_to_Biometric_Verification_Based_on_Human_Body_Communication_in_Wearable_Devices/link/5a4e5aacaca272c88278b5b7/download.

Yadav, Umang et al., "Evaluation of PPG Biometrics for Authentication in different states", Cryptography and Security—Computer Vision and Pattern Recognition—Signal Processing, Dec. 2017, Arxiv, https://www.researchgate.net/publication/312207310_An_Approach_to_Biometric_Verification_Based_on_Human_Body_Communication_in_Wearable_Devices/link/5a4e5aacaca272c88278b5b7/download.

CONTINUOUSLY VALIDATING A USER DURING AN ESTABLISHED AUTHENTICATED SESSION USING PHOTOPLETHYSMOGRAM AND ACCELEROMETER DATA

PRIORITY CLAIM

This U.S. patent application claims priority under 35 U.S.C. § 119 to: Indian patent application no. 202021014033, filed on Mar. 30, 2020. The entire contents of the aforementioned application are incorporated herein by reference.

TECHNICAL FIELD

The embodiments herein generally relate session authentication and validation and, more particularly, to a method and system for continuously validating a user during an established authenticated session using Photoplethysmogram (PPG) and accelerometer data.

BACKGROUND

Round the clock availability of internet, advancement in device and communication technology, and availability of devices such as mobile phones or smart phones enables providing multitude of digital services, many of which require to be highly confidential and/or secured such as banking transaction service, applications or platforms providing sensitive data access/modification and so on. Thus, mere authentication of a user to establish the session may not suffice but continuously validating the user throughout the session is critical to ensure completely secured digital service. One time passwords (OTPs), biometrics such as iris, fingerprint and the like are tested conventional methods used for session authentication. Research attempts have used physiological signal, which can uniquely identify the authenticated user, for continuous validation of the user during the session.

Wearable devices, such as smart watches, fitness bands and the like, are equipped with PPG sensors, accelerometer, gyroscope and so on to provide sensing of user specific physiological signals that can be used for session validation. There are attempts that limit use of PPG signals for session authentication, however, these approaches do not focus on continuous session validation. Few literature works attempt usage of PPG signal for session continuity check. One of the works in the art utilized parameters derived from PPG signal such as Hear Rate Variability (HRV). Deriving the HRV from PPG requires eliminating of motion artifacts overriding a PPG signal. Further, the derived HRV is analyzed by a Machine Learning (ML) model to validate the user. However, eliminating motion artifacts is continuous task as majority of the PPG signal has high presence of motion artifacts. Further, deriving HRV from the PPG signal adds on additional processing time. Furthermore, training of ML model is computationally intensive task for low power wearables or the handheld devices. Such ML model-based approaches require additional training exercise and accuracy of the results are largely dependent on the training data used. Further, some existing approaches generate missing PPG data for continuous validation using synthetic data generation and not the true PPG data, which further affects the accuracy of any end result. While some existing methods derive features from PPG signal to be further processed for user validation.

SUMMARY

Embodiments of the present disclosure present technological improvements as solutions to one or more of the above-mentioned technical problems recognized by the inventors in conventional systems.

For example, in one embodiment, a method for continuously validating a user during an established authenticated session using Photoplethysmogram (PPG) and accelerometer data. The method comprises detecting the established authenticated session of a user, wherein the user is authenticated during a session establishment process using an authentication mechanism.

Further, the method comprises simultaneously receiving a PPG signal from a PPG sensor of a wearable device worn by the authenticated user.

Further, the method comprises preprocessing the PPG signal to determine a set of PPG segments with minimal motion artifact presence, wherein each of the set of PPG segments is greater than a preset window size, and wherein the preprocessing selects portions of the received PPG signal corresponding to portions of an synchronized accelerometer data received from an accelerometer sensor of the wearable device, and the selected portions of the synchronized accelerometer data indicate minimal motion artifacts based on a preset motion artifact threshold.

Further, the method comprises selecting a first PPG segment among the set of PPG segments as a reference segment, post detection of the established authenticated session; and a succeeding segment to the first segment as a test segment.

Furthermore, the method comprises determining a number of PPG pulses (I), with pulse ($p_i$), where i∈1, 2, ..., I−1) present in the test segment and a number of PPG pulses (J) with pulse ($p_j$), where j∈1, 2, ..., J−1) present in the reference segment by applying trough to trough detection.

Furthermore, the method comprises stretching in time and normalize in area each pulse ($p_j$) among the number of PPG pulses (I) and each pulse ($p_i$) among the number of PPG pulses (J).

Furthermore, the method comprises performing a template matching between the stretched PPG pulses (I) of the test segment and the stretched PPG pulses (J) of the reference segment by: computing a minimum distance vector $d_{test}[i]$, of pulse $p_i$ for all i∈1, 2, ..., I−1, by comparing with each of the PPG pulses (J) using a Euclidean distance similarity measure; and computing a minimum distance vector $d_{ref}[j]$, of pulse $p_j$ for all j ∈ 1, 2, ..., J−1 by comparing with each of the number of PPG pulses (I) using the Euclidean distance similarity measure, when j≠i;

Furthermore, the method comprises computing distributions for all $d_{test}[i]$ and $d_{ref}[j]$; and validating the user participating in the established authenticated session if a validation criterion is satisfied, wherein the validation criterion maps the test segment to the reference segment if percentage of distances in $d_{test}$, for $d_{test}$>a distance criterial ($d_1$), is less than a percentage based threshold ($t_2$).

Furthermore, the method comprises reselecting the test segment as the reference segment if the validation criterion is satisfied and repeat the steps of continuously validating the user during the established authenticated session.

Furthermore, the method comprises invalidating the user corresponding to the test segment if the validation criterion is dissatisfied; close the established authenticated session; request the user to reauthenticate using the authentication mechanism to re-establish an authenticated session; and repeat the steps of continuously validating the user during the re-established authenticated session based on a reference segment and a test segment identified for the re-established authenticated session.

In another aspect, a system for continuously validating an authenticated user during an established authenticated session using Photoplethysmogram (PPG) and accelerometer data is provided. The system comprises a memory storing instructions; one or more Input/Output (I/O) interfaces; and one or more hardware processors coupled to the memory via the one or more I/O interfaces, wherein the one or more hardware processors are configured by the instructions to detect the established authenticated session of a user, wherein the user is authenticated during a session establishment process using an authentication mechanism.

Furthermore, the one or more hardware processors are configured to simultaneously receive a PPG signal from a PPG sensor of a wearable device worn by the authenticated user.

Further, the one or more hardware processors are configured to preprocess the PPG signal to determine a set of PPG segments with minimal motion artifact presence, wherein each of the set of PPG segments is greater than a preset window size, and wherein the preprocessing selects portions of the received PPG signal corresponding to portions of an synchronized accelerometer data received from an accelerometer sensor of the wearable device, and the selected portions of the synchronized accelerometer data indicate minimal motion artifacts based on a preset motion artifact threshold.

Further, the method comprises the one or more hardware processors are configured to select a first PPG segment among the set of PPG segments as a reference segment, post detection of the established authenticated session; and a succeeding segment to the first segment as a test segment.

Furthermore, the one or more hardware processors are configured to determine a number of PPG pulses (I), with pulse ($p_i$), where i∈1, 2, . . . , I−1) present in the test segment and a number of PPG pulses (J) with pulse ($p_j$), where j∈1, 2, . . . , J−1) present in the reference segment by applying trough to trough detection;

Furthermore, the one or more hardware processors are configured to stretch in time and normalize in area each pulse ($p_j$) among the number of PPG pulses (I) and each pulse ($p_i$) among the number of PPG pulses (J).

Furthermore, the one or more hardware processors are configured to perform a template matching between the stretched PPG pulses (I) of the test segment and the stretched PPG pulses (J) of the reference segment by: computing a minimum distance vector $d_{test}[i]$, of pulse $p_i$ for all i∈1, 2, . . . , I−1, by comparing with each of the PPG pulses (J) using a Euclidean distance similarity measure; and computing a minimum distance vector $d_{ref}[j]$, of pulse $p_j$ for all j∈1, 2, . . . , J−1 by comparing with each of the number of PPG pulses (I) using the Euclidean distance similarity measure, when j≠i;

Furthermore, the one or more hardware processors are configured to compute distributions for all $d_{test}[i]$ and $d_{ref}[j]$; and validate the user participating in the established authenticated session if a validation criterion is satisfied, wherein the validation criterion maps the test segment to the reference segment if percentage of distances in $d_{test}$, for $d_{test} > a$ distance criterial ($d_1$), is less than a percentage based threshold ($t_2$).

Furthermore, the one or more hardware processors are configured to reselect the test segment as the reference segment if the validation criterion is satisfied and repeat the steps of continuously validating the user during the established authenticated session.

Furthermore, the one or more hardware processors are configured to invalidate the user corresponding to the test segment if the validation criterion is dissatisfied; close the established authenticated session; request the user to reauthenticate using the authentication mechanism to re-establish an authenticated session; and repeat the steps of continuously validating the user during the re-established authenticated session based on a reference segment and a test segment identified for the re-established authenticated session.

In yet another aspect, there are provided one or more non-transitory machine readable information storage mediums comprising one or more instructions, which when executed by one or more hardware processors causes a method for continuously validating an authenticated user during an established authenticated session using Photoplethysmogram (PPG) and accelerometer data. The method comprises detecting the established authenticated session of a user, wherein the user is authenticated during a session establishment process using an authentication mechanism.

Further, the method comprises simultaneously receiving a PPG signal from a PPG sensor of a wearable device worn by the authenticated user.

Further, the method comprises preprocessing (206), by the one or more hardware processors, the PPG signal to determine a set of PPG segments with minimal motion artifact presence, wherein each of the set of PPG segments is greater than a preset window size, and wherein the preprocessing selects portions of the received PPG signal corresponding to portions of an synchronized accelerometer data received from an accelerometer sensor of the wearable device, and the selected portions of the synchronized accelerometer data indicate minimal motion artifacts based on a preset motion artifact threshold.

Further, the method comprises selecting a first PPG segment among the set of PPG segments as a reference segment, post detection of the established authenticated session; and a succeeding segment to the first segment as a test segment.

Furthermore, the method comprises determining a number of PPG pulses (I), with pulse ($p_i$), where i∈1, 2, . . . , I−1) present in the test segment and a number of PPG pulses (J) with pulse ($p_j$), where j∈1, 2, . . . , J−1) present in the reference segment by applying trough to trough detection;

Furthermore, the method comprises stretching in time and normalize in area each pulse ($p_j$) among the number of PPG pulses (I) and each pulse ($p_i$) among the number of PPG pulses (J).

Furthermore, the method comprises performing a template matching between the stretched PPG pulses (I) of the test segment and the stretched PPG pulses (J) of the reference segment by: computing a minimum distance vector $d_{test}[i]$, of pulse $p_i$ for all i∈1, 2, . . . , I−1, by comparing with each of the PPG pulses (J) using a Euclidean distance similarity measure; and computing a minimum distance vector $d_{ref}[j]$, of pulse $p_j$ for all j∈1, 2, . . . , J−1 by comparing with each of the number of PPG pulses (I) using the Euclidean distance similarity measure, when j≠i;

Furthermore, the method comprises computing distributions for all $d_{test}[i]$ and $d_{ref}[j]$; and validating the user participating in the established authenticated session if a validation criterion is satisfied, wherein the validation criterion maps the test segment to the reference segment if percentage of distances in $d_{test}$, for $d_{test}>$a distance criterial ($d_1$), is less than percentage based threshold ($t_2$).

Furthermore, the method comprises reselecting the test segment as the reference segment if the validation criterion is satisfied and repeat the steps of continuously validating the user during the established authenticated session.

Furthermore, the method comprises invalidating the user corresponding to the test segment if the validation criterion is dissatisfied; close the established authenticated session; request the user to reauthenticate using the authentication mechanism to re-establish an authenticated session; and repeat the steps of continuously validating the user during the re-established authenticated session based on a reference segment and a test segment identified for the re-established authenticated session.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

Figure 1:
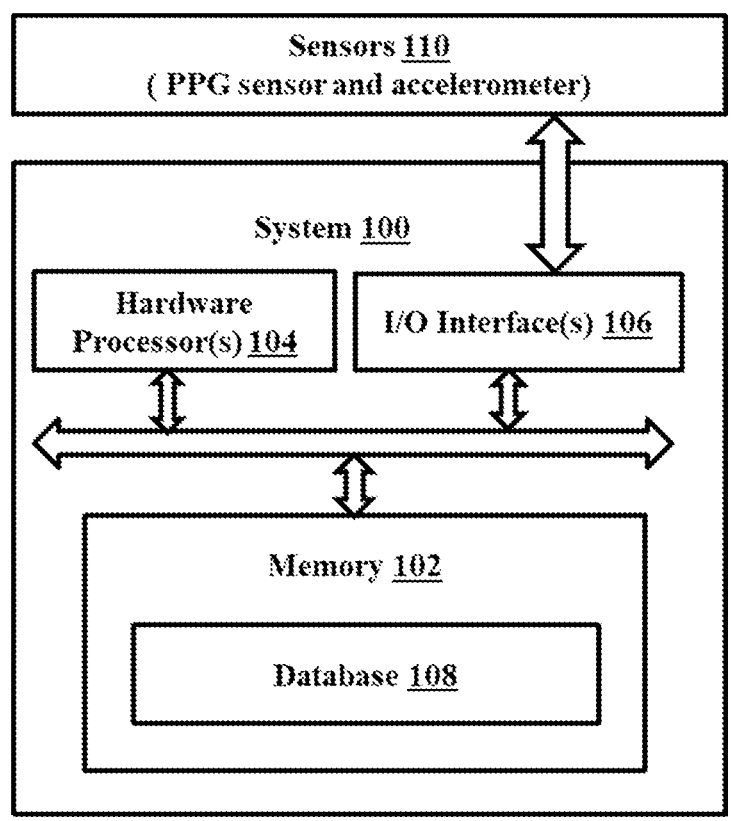
FIG. 1 is a functional block diagram of a system for continuously validating a user during an established authenticated session using Photoplethysmogram (PPG) and accelerometer data, in accordance with some embodiments of the present disclosure.

It should be appreciated by those skilled in the art that any block diagrams herein represent conceptual views of illustrative systems and devices embodying the principles of the present subject matter. Similarly, it will be appreciated that any flow charts, flow diagrams, and the like represent various processes which may be substantially represented in computer readable medium and so executed by a computer or processor, whether or not such computer or processor is explicitly shown.

DETAILED DESCRIPTION OF EMBODIMENTS

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

PPG based biometric systems have proven to be feasible in the past research works. Umang Yadav et al. evaluated such schemes over different user activities. In most of the research works, authors have proposed signal processing techniques along with various fiducial (time-domain, statistical), as provided by Abhijit Sarkar et. al in 'Biometric authentication using photoplethysmography signals.' Some works such as from Sun-Woo Lee et. al on 'Wearable Bio-Signal (PPG)-Based Personal Authentication' work with non-fiducial (based on the transform of actual PPG data) feature extractions. The extracted features are used in one-class or binary classification with machine learning techniques. Authentication using PPG template based matching through distance computations have been mentioned in work by Jorge Sancho et. al on 'Biometric authentication using the PPG: a long-term feasibility study. However, the template based approach used by Sancho et. al utilizes a complicated process, requiring more computation as it uses a percentile-based threshold to ensure that dicrotic notches are not identified as troughs.

Embodiments herein provide a method and system for continuously validating a user during an established authenticated session using Photoplethysmogram (PPG) and accelerometer data. The method disclosed herein utilizes less computation intensive template based matching approach to validate the user across the established authenticated session, interchangeably referred herein as established session. Unlike, Sancho et. al, the method comprises preprocessing a PPG data or PPG signal acquired from a wearable device worn by the user to identify segments of negligible motion. A first segment, after authentication using conventional authentication mechanism, serves as the initial reference. The chosen segments are then tested one by one with respect to the reference. If the templates in a segment match those of the reference, it is updated as the new reference, else a re-authentication is triggered.

Referring now to the drawings, and more particularly to FIGS. 1 through 5B, where similar reference characters denote corresponding features consistently throughout the figures, there are shown preferred embodiments and these embodiments are described in the context of the following exemplary system and/or method.

FIG. 1 is a functional block diagram of a system 100 for continuously validating a user during an established authenticated session using Photoplethysmogram (PPG) and accelerometer data, in accordance with some embodiments of the present disclosure.

In an embodiment, the system 100 includes a processor(s) 104, communication interface device(s), alternatively referred as input/output (I/O) interface(s) 106, and one or more data storage devices or a memory 102 operatively coupled to the processor(s) 104. The system 100, may be alternatively referred herein as system or system 100. The system 100 with one or more hardware processors is configured to execute functions of one or more functional blocks of the system 100.

Referring to the components of system 100, in an embodiment, the processor(s) 104, can be one or more hardware processors 104. In an embodiment, the one or more hardware processors 104 can be implemented as one or more microprocessors, microcomputers, microcontrollers, digital signal processors, central processing units, state machines, logic circuitries, and/or any devices that manipulate signals based on operational instructions. Among other capabilities, the one or more hardware processors 104 are configured to fetch and execute computer-readable instructions stored in the memory 102. In an embodiment, the system 100 can be implemented in a variety of computing systems including laptop computers, notebooks, handheld devices such as mobile phones, alternatively referred as smart phones or User Equipment's (UEs), tablets, personal digital Assistants (PDAs), cloud servers and the like.

The I/O interface(s) 106 can include a variety of software and hardware interfaces, for example, a web interface, a graphical user interface for various viewing of messages displayed in the viewports, and the like and can facilitate multiple communications within a wide variety of networks N/W and protocol types, including wired networks, for example, LAN, cable, etc., and wireless networks, such as WLAN, cellular, or satellite. In an embodiment, the I/O interface (s) 106 can include one or more ports for connecting a number of devices (nodes) of the system 100 to one another or to another server. The I/O interface 106 can receive a PPG signal and the accelerometer data from PPG sensors and accelerometer of any wearable device, such as a smart phone or a fitness device connected to the system 100. The system 100 then is configured to process the received PPG signal and the accelerometer data for continuously validating the user during the established session. In an embodiment, the wearable device such as the smart phone or the fitness device itself can perform functions of the system 100 to validate the user.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. The memory 102 may comprise a plurality of modules (not shown), when implemented by the system 100 to implement the functions for continuously validating the user during the established session using the PPG signal and the accelerometer data. Further, the memory 102 may include a database 108, which may store received PPG signals, accelerometer data, plurality of segments of the received PPG signal, preprocessed PPG segments with minimal motion artifacts, a reference segment, test segments and so on. Thus, the memory 102 may comprise information pertaining to input(s)/output(s) of each step performed by the processor(s) 104 of the system 100 and methods of the present disclosure.

In an embodiment, the database 108 may be external (not shown) to the system 100 and coupled to the system via the I/O interface 106. Functions of the components of system 100 are explained in conjunction with flow diagram of FIGS. 2A, 2B and 2C and graphical representations/experimental analysis depicted in FIG. 3 through FIG. 5B.

Figure 2A:
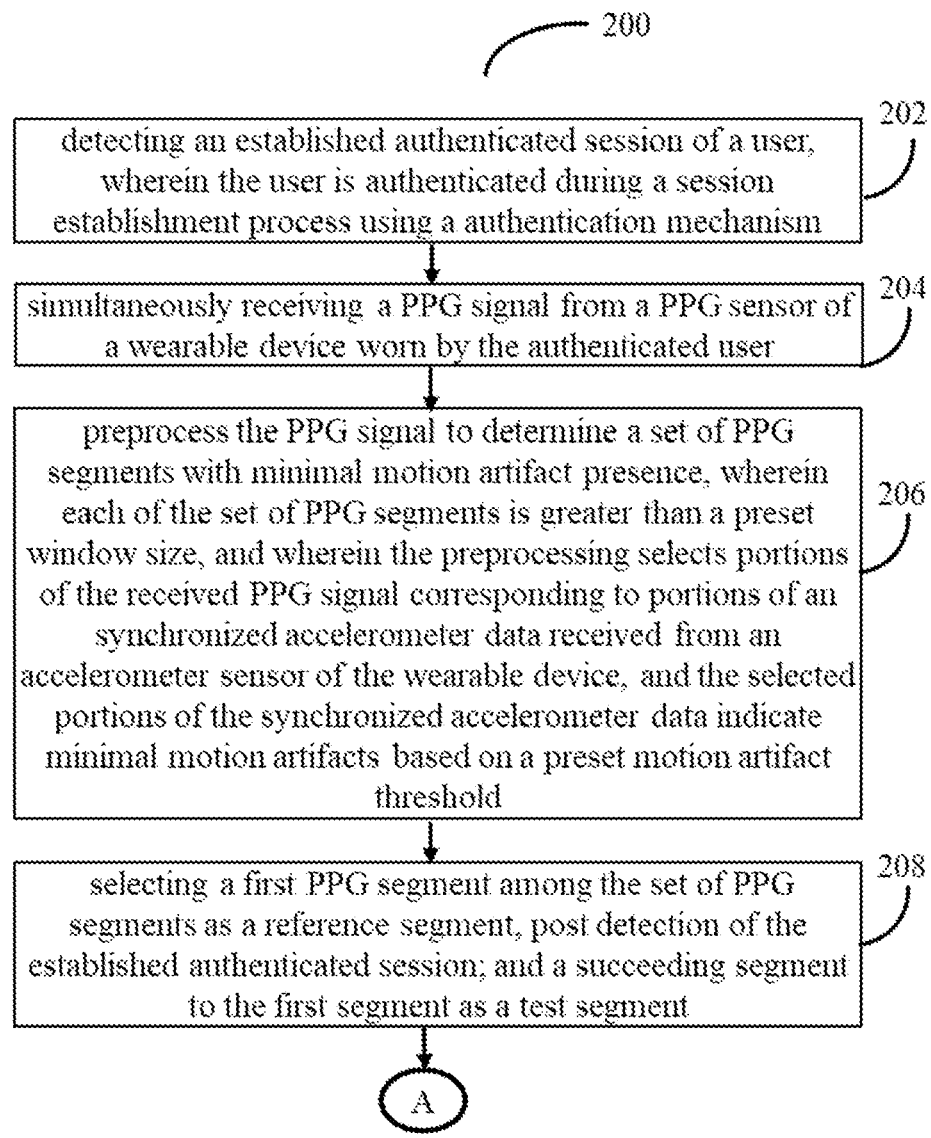
FIGS. 2A, 2B and 2C depict a flow diagram illustrating a method for continuously validating a user during an established authenticated session using Photoplethysmogram (PPG) and accelerometer data using the system of FIG. 1, in accordance with some embodiments of the present disclosure.
Figure 2B:
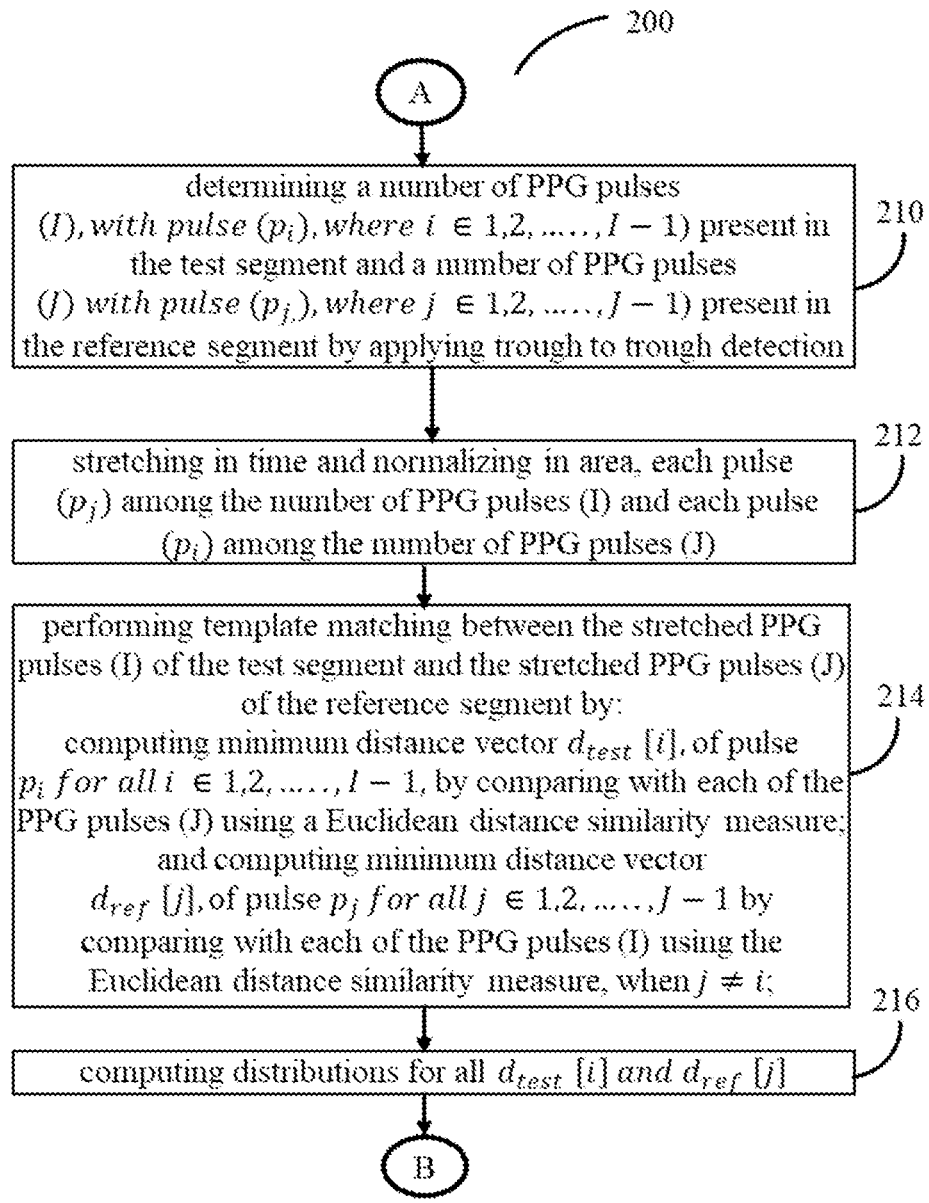
Figure 2C:
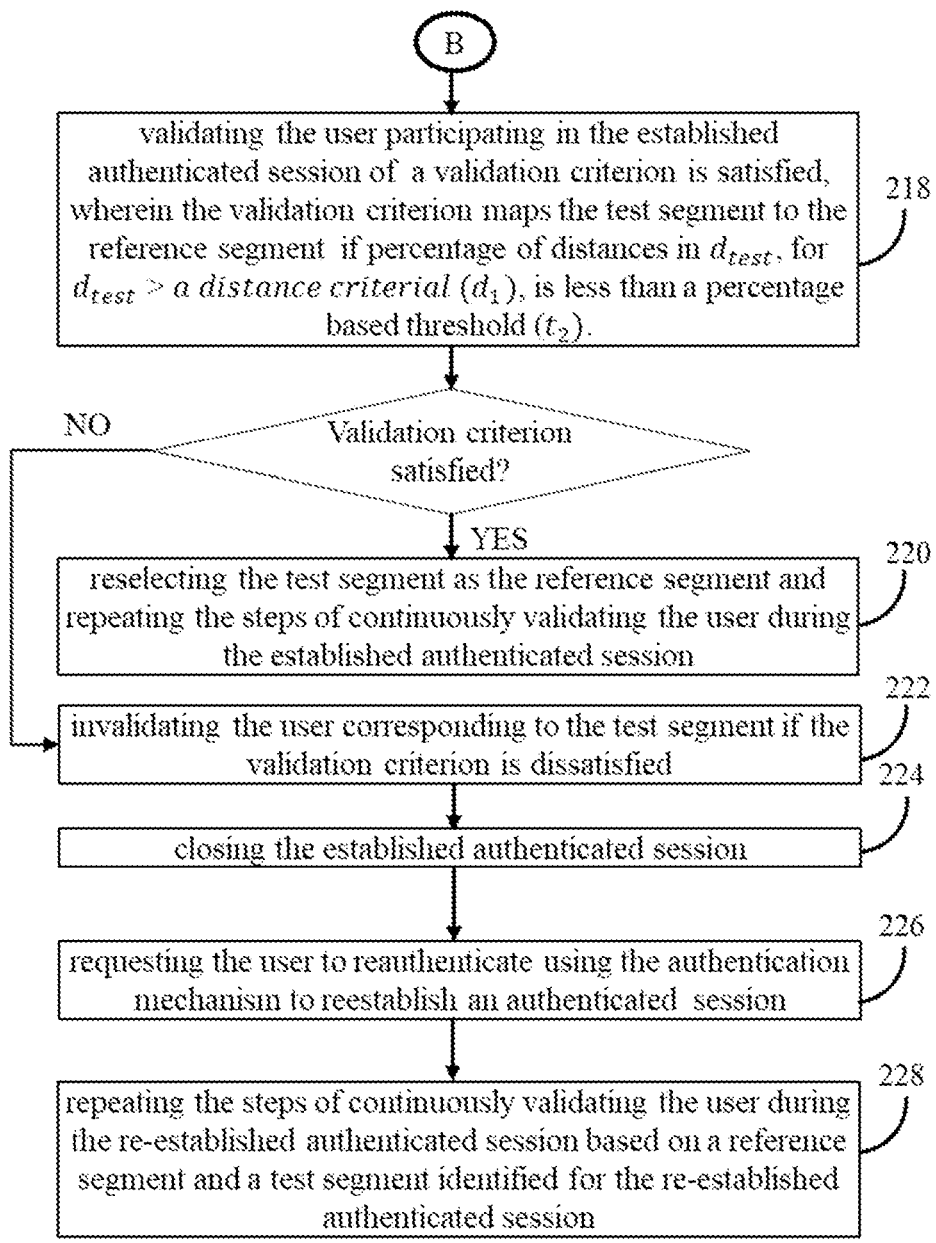

FIGS. 2A, 2B and 2C depict a flow diagram illustrating a method for continuously validating the user during the established authenticated session using Photoplethysmogram (PPG) and accelerometer data using the system of FIG. 1, in accordance with some embodiments of the present disclosure.

In an embodiment, the system 100 comprises one or more data storage devices or the memory 102 operatively coupled to the processor(s) 104 and is configured to store instructions for execution of steps of the method 200 by the processor(s) or one or more hardware processors 104. The steps of the method 200 of the present disclosure will now be explained with reference to the components or blocks of the system 100 as depicted in FIG. 1 and the steps of flow diagram as depicted in FIGS. 2A through 2C. Although process steps, method steps, techniques or the like may be described in a sequential order, such processes, methods and techniques may be configured to work in alternate orders. In other words, any sequence or order of steps that may be described does not necessarily indicate a requirement that the steps to be performed in that order. The steps of processes described herein may be performed in any order practical. Further, some steps may be performed simultaneously.

In an example set up, implementation of the method 200 disclosed herein, can be triggered by the system 100 whenever any user initiates a session establishment request through the system 100 such as a bank transaction request initiated by the user from his smartphone. The user initiating the request is required to wear a wearable device equipped with a plurality of sensors 110, comprising at least a PPG sensor and a accelerometer. As mentioned, in an embodiment, the system 100 itself can be the wearable device capable of implementing the method and process acquired sensor data (the PPG signal and the accelerometer data) for user validation. In an embodiment any master device of the wearable device such as a smartphone, a tablet, a laptop, a server and the like can receive the sensor data via the I/O interface 106 from the wearable device and process the sensor data for validating the user during the session. In one implementation, as soon as a user request is received for session establishment, the following checks can be done: 1) Is the wearable device active 2) Are the PPG signal and accelerometer signal available. Only upon such confirmation the user may optionally enable continuous validation of the session to be established for the session establishment request.

Once the session establishment request is processed, referring now to the steps of the method 200, at step 202, one or more hardware processors 104 are configured to detect an established authenticated session of the user, wherein the user is authenticated during a session establishment process using an authentication mechanism. The session establishment is in accordance with corresponding conventional session protocols. Any conventional well tested authentication mechanism can be used for first authentication to establish a secure session. Such mechanisms include but are not limited to fingerprint recognition, iris recognition, face recognition, different types of password based authentication and the like.

Figure 3A:
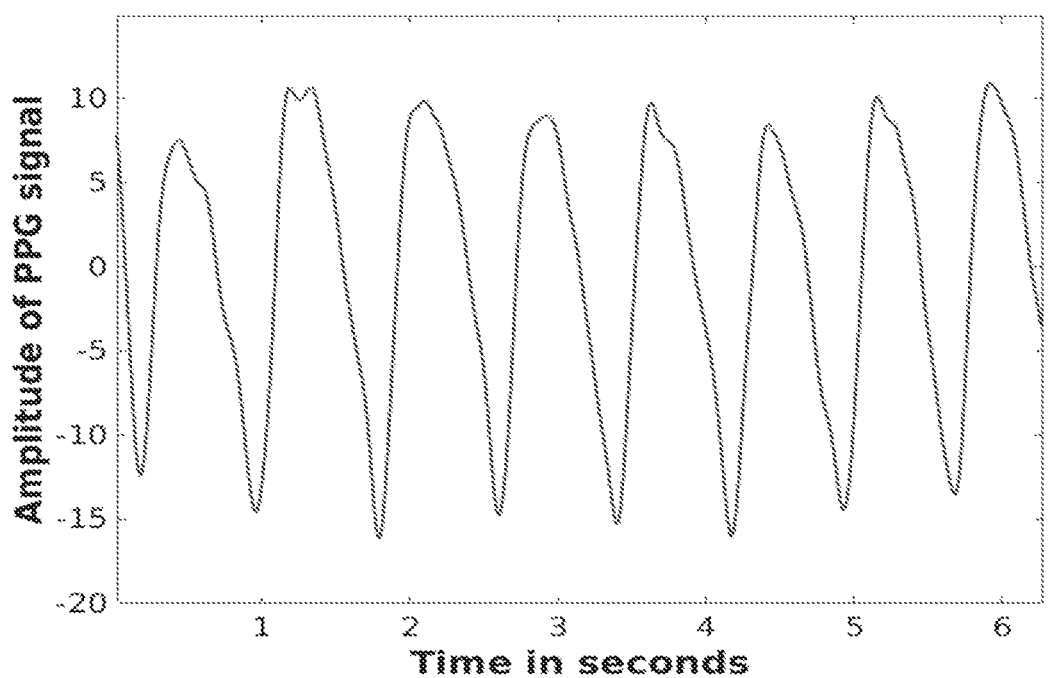
FIG. 3A and FIG. 3B illustrate a PPG signal from a PPG sensor of wearable device with and without presence of motion artifacts respectively, wherein the system of FIG. 1 detects segments of PPG signal without the motion artifacts, in accordance with some embodiments of the present disclosure.
Figure 3B:
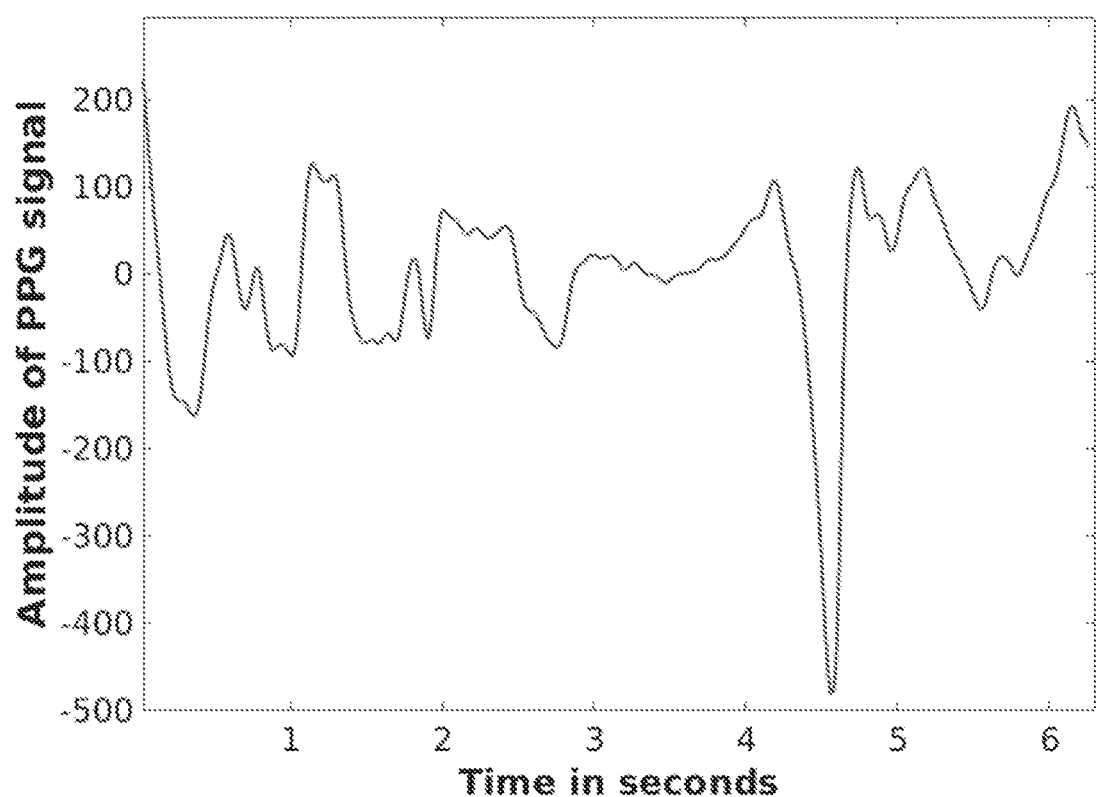

During the session establishment process, at step 204, the one or more hardware processors 104 are configured to simultaneously receive a PPG signal from the PPG sensor (sensor 110) of the wearable device worn by the authenticated user. Simultaneously, accelerometer data from the accelerometer (sensor 110), which is time synchronized with the PPG signal, is received by the system 100. The received PPG signal is segmented into a plurality of PPG segments of a fixed time window. In an example implementation the fixed time window chosen is of 30 seconds, which provides sufficient PPG data for processing to perform enable continuous user validation during an ongoing session. The received PPG signal, since is obtained from the wearable device, generally worn on the hand by the user, comprises considerable overriding motion artifacts on the PPG data, which is adds considerable noise to the PPG data present over larger time span of the received PPG signal. Thus, instead of following an approach of filtering the motion artifacts, the method 200 disclosed utilizes an approach to select only those PPG segments for further processing, which have minimal motion artifacts. This reduces time and computation required for generating a clean PPG signal. FIG. 3A and FIG. 3B illustrate a PPG signal from the PPG sensor of the wearable device with and without presence of motion artifacts respectively, wherein the system of FIG. 1 detects segments of PPG signal without the motion artifacts for further processing. In the approximately 50 hours of real-life data collected, segments of unusable PPG data (with presence of considerable motion artifacts were almost 10 minutes long. Thus, the method disclosed herein, does not spend computational resources in filtering the motion artifacts, instead those segments where the motion is negligible are identified for matching and identifying the same user.

Thus, at step 206 of the method 200, the one or more hardware processors 104 are configured to preprocess the PPG signal to determine a set of PPG segments with minimal motion artifact presence, wherein each of the set of PPG segments is greater than a preset window size, and wherein the preprocessing selects portions of the received PPG signal corresponding to portions of an synchronized accelerometer data received from an accelerometer sensor of the wearable device, and the selected portions of the synchronized accelerometer data indicate minimal motion artifacts based on a preset motion artifact threshold. Other preset window sizes can also be used such as 10 second window can also be one among multiple option. Thus, any preset window size can be selected that best satisfies the continuous monitoring requirement. The preprocessing compares the received PPG signal against each sample among a plurality of samples of the synchronized accelerometer data received from the accelerometer of the wearable device based on the preset motion artifact threshold to determine the set of PPG segments.

Preprocessing of the PPG Segments or Filtering of the PPG Segments Received from Wearable Device to Discard Motion Artifacts:

It can be understood that the accelerometer data provides presence of motion of user's body part, on which the wearable device is worn. This data provides the reference motion signal of the user, used for determining heavy motion artifact in the PPG segments and accordingly discarding the corresponding PPG signal.

Consider T seconds of the accelerometer data (over the three axes i.e. Accx, Accy and Accz). Let Fs Hz be the sampling frequency of the system 100 collating this data. The number of sample points for accelerometer are T×Fs. Magnitude of acceleration value across x, y, z axes is computed as:

$$|Acc| = \sqrt{Accx^2 + Accy^2 + Accz^2} \quad (1)$$

Data from first 10 sample points are ignored. For each sample point after the 10th sample point, difference between the accelerometer value at the considered sample point and each of the previous sample points are computed. Thereafter, all computed differences are analyzed to check if are lesser than a threshold value Th (which is chosen after visual examination of the accelerometer and PPG signal by an expert, indicating acceptable minimal presence of motion artifacts in a PPG signal/segment). If the computed differences are greater than the threshold value Th, a next sample point is chosen, and the above computation and thresholding is repeated. Further, one multiple sample points are processed, the PPG data for the time interval where the consecutive computed differences are less the threshold value Th are selected as minimal motion artifact PPG segments, only if the time interval considered is greater than the preset window size of 30 seconds.

Upon identification of set of PPG segments, at step 208 of the method 200, the one or more hardware processors 104 are configured to select (i) a first PPG segment among the set of PPG segments as a reference segment, post detection of the established session and (ii) a succeeding segment to the first segment as a test segment.

At step 210 of the method 200, the one or more hardware processors 104 are configured to determine a number of PPG pulses (I), with pulse ($p_i$), where (i∈ 1, 2, . . . , I−1) present in the test segment and a number of PPG pulses (J) with pulse ($p_j$), where (j∈ 1, 2, . . . , J−1) present in the reference segment by applying trough to trough detection. In each template (i.e., the segment), the troughs are first identified. Next, trough-to-trough PPG data is extracted such that each pulse has a systolic and a diastolic peak.

Figure 4:
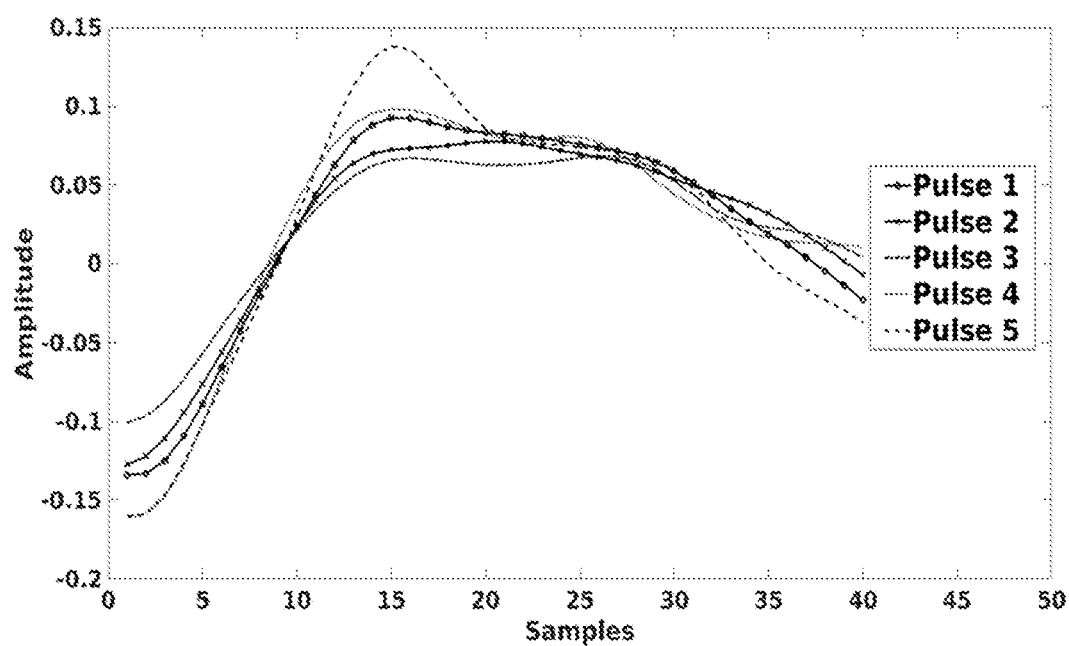
FIG. 4 depicts normalized PPG pulses within a PPG segment, in accordance with some embodiments of the present disclosure.

At step 212 of the method 200, the one or more hardware processors 104 are configured to stretch in time and normalize in area pulse ($p_j$) among the number of PPG pulses (I) and each pulse ($p_j$) among the number of PPG pulses (J). The individual PPG pulses are then stretched in time to a nominal width of 625 milliseconds (40 samples at a sampling rate of 64 Hz) and normalized in area. FIG. 4 depicts normalized PPG pulses within a PPG segment, in accordance with some embodiments of the present disclosure.

At step 214 of the method 200, the one or more hardware processors 104 are configured to perform template matching between the stretched PPG pulses (I) of the test segment and the stretched PPG pulses (J) of the reference segment by:
  a) computing a minimum distance vector $d_{test}[i]$, of pulse $p_i$ for all i∈ 1, 2, . . . , I−1, by comparing with each of the PPG pulses (J) using a Euclidean distance similarity measure; and
  b) computing a minimum distance vector $d_{ref}[j]$, of pulse $p_j$ for all j∈ 1, 2, . . . , J−1 by comparing with each of the PPG pulses (I) using the Euclidean distance similarity measure, when j≠i.

At step 216 of the method 200, the one or more hardware processors 104 are configured to compute distributions for all $d_{test}[i]$ and $d_{ref}[j]$.

At step 218 of the method 200, the one or more hardware processors 104 are configured to validate the user participating in the established authenticated session of a validation criterion is satisfied, wherein the validation criterion maps the test segment to the reference segment if percentage of distances in $d_{test}$, for $d_{test}$>a distance criterial ($d_1$), is less than a percentile based threshold ($t_2$).

For, I pulses, $p_i$ for all i∈ 1, 2, . . . , I−1, in the test segment and J pulses, $p_j$ for all j∈ 1, 2, . . . , J−1, in the reference segment, typically, I, J are in the range of [30, 40] pulses. The number of pulses depend on the preset window size that is selected. For the $i^{th}$ pulse, its minimum distance from the reference is calculated as:

$$d_{test}[i] = \min_{j \in \{0, \ldots, J-1\}} dist(p_i, r_j) \quad (2)$$

where, dist (x, y) is the Euclidean distance metric. The distances $d_{ref}[j]$ are also computed as in equation (1) with j≠i.

Next, the distributions of the distances $d_{ref}$ and $d_{test}$ are computed. To determine if the test segment belongs to the same user as the reference segment, initially a first threshold $t_1$ percentile based threshold) is needed. Further, $d_1$ is computed such that $t_1$-percentile of the distance vector in $d_{ref}$. The test segment is treated to be of the same user if the percentage of distances in $d_{test}$·d1>d1 is less than the percentage based threshold (also refereed as a second threshold $t_2$). Such a test segment is treated as the reference segment for the computation with next segment.

Relative thresholds $t_1$ and $t_2$ are application-specific. Let $d_1$ be the $t_1$-percentile ($t_1 \approx 90$) of the distance distribution of the reference itself. If fewer than $t_2(\approx 10)$ percent of the distances of the next segment>$d_1$, the session is maintained, and this segment is updated as the reference.

Referring back to steps of method 200, at step 220, the one or more hardware processors 104 are configured to reselect the test segment as the reference segment if the validation criterion is satisfied and the steps of continuously validating the user during the established authenticated session are repeated.

However, if the validation criterion is unsatisfied, at step 222 the one or more hardware processors 104 are configured to invalidate the user corresponding to the test segment, at step 224, close the established session; at step 226, request the user to reauthenticate using the conventional authentication mechanism to re-establish the session; and at step 228 repeat the steps of continuously validating the user during the re-established authenticated session based on a reference segment and a test segment identified for the re-established authenticated session.

Figure 5A:
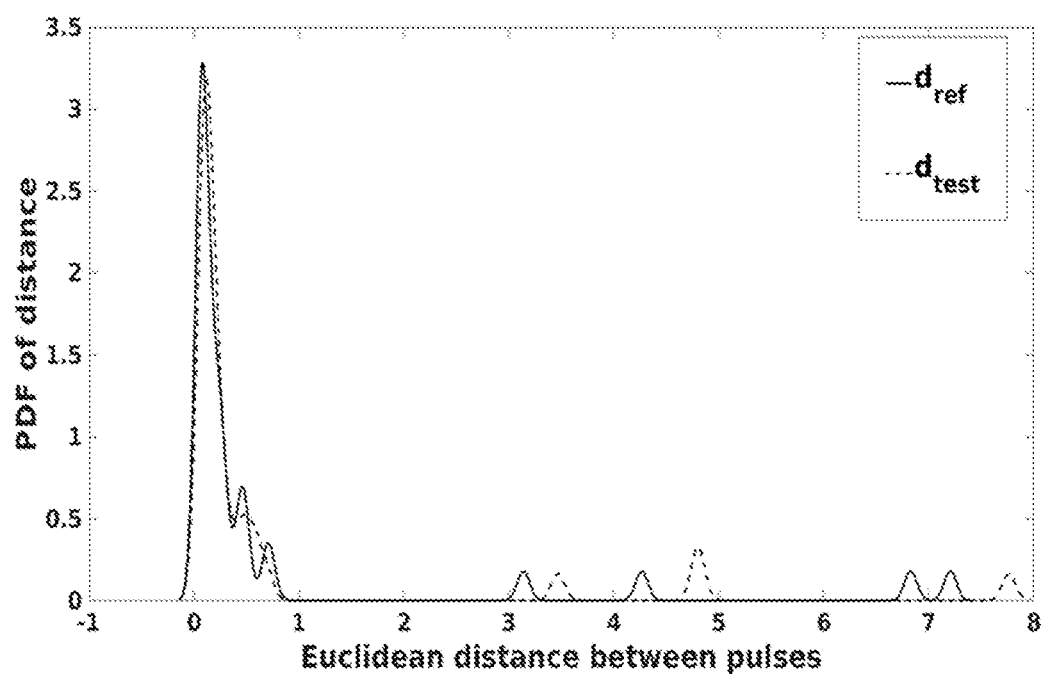
FIG. 5A and FIG. 5B depict distributions of distances with of test PPG segment with respect to a reference PPG segment for a valid user and an invalid user respectively, in accordance with some embodiments of the present disclosure.
Figure 5B:
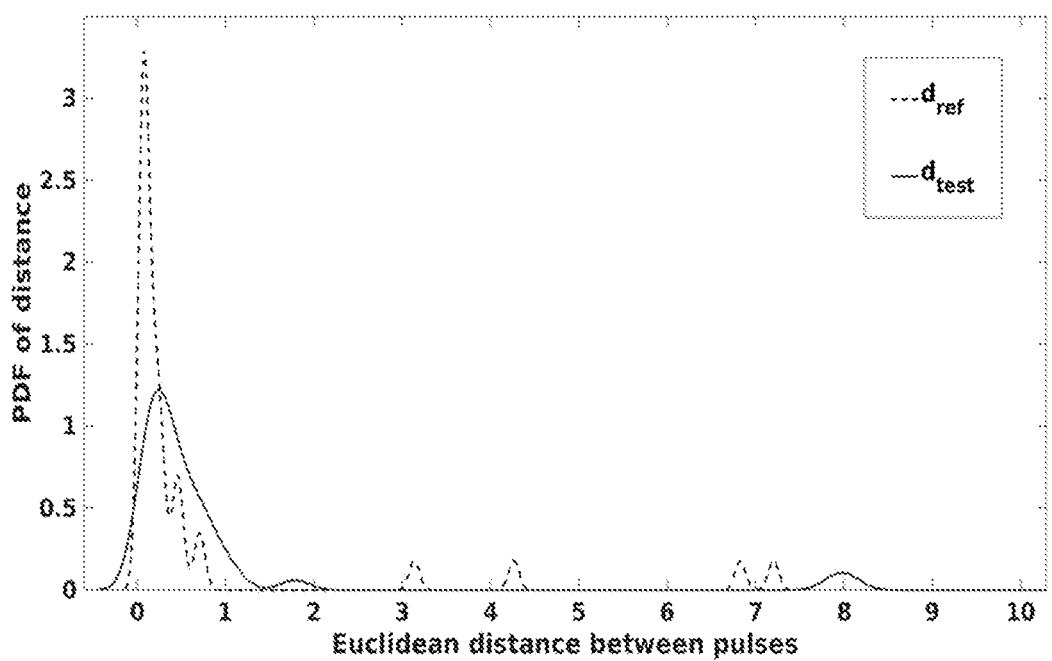

FIG. 5A and FIG. 5B depict distributions of distances of test PPG segment with respect to a reference PPG segment for a valid user and an invalid user respectively, in accordance with some embodiments of the present disclosure.

Evaluation and Results: Dataset used: Seven consenting participants (2 female, 5 male) wore the Empatica E4 Wearable™ on a working day. The wristband recorded accelerometer, PPG, electro-dermal activity, and temperature data. Herein, 7 hours of anonymized accelerometer and PPG data are used.

Evaluation criteria: In a deployment scenario used, i.e., continuously validating the user using the PPG data and the accelerometer data, the minimum False-Negative (FN) rate is a natural evaluation criterion. Thus, a grid search is performed to obtain the values of $t_1$ and $t_2$ that minimize the FN. Further, in this scenario, it is acceptable to optimize these values per user. In order to compare with state of the art techniques, also reported are the rates at which FN and False Positive (FP) rate are equal, i.e., Equal Error Rate (EER). The EER measure was proposed by Jorge Sancho et. al. In this scenario herein, a grid search is performed to obtain the values of $t_1$ and $t_2$ that minimize the EER. In a deployment scenario, re-authentication may be made mandatory on watch removal, and it is thus acceptable to minimize FN and EER independently.

Results: Table 1 shows the minimum FN for the seven users used. From the table 1, it can be seen that, across users, the values of $t_1$ and $t_2$ at the minimum FN ranges from 60 to 90-percentile, and those of $t_2$ range from 9 to 13%. Both ranges respectively cover high and low values, which is as expected. For the same users, the EER ranges from 0.41% to 10% (Table 2), which is in the range reported by Jorge Sancho et. al. Note that all the results in Jorge Sancho et. al are collected in lab environment, i.e. with very little motion. The corresponding ranges for $t_1$ and $t_2$ are 80 to 90 percentile and 7 to 11% respectively and are as expected.

TABLE 1

Minimum False Negative rates (%) and the corresponding thresholds $t_1$ (percentile) and $t_2$ (percentage) for seven users.

| UserID | FN | $t_1$ | $t_2$ |
|---|---|---|---|
| 1 | 0.41 | 89.4 | 9 |
| 2 | 0.41 | 93.45 | 13 |
| 3 | 0.41 | 58.35 | 13 |
| 4 | 0.83 | 94.8 | 11 |
| 5 | 0.41 | 93.45 | 9 |
| 6 | 0.41 | 97.5 | 9 |
| 7 | 0.41 | 86.7 | 13 |

TABLE 2

Equal error rates (%) and the corresponding thresholds $t_1$ (percentile) and $t_2$ (percentage) for seven users.

| UserID | EER | $t_1$ | $t_2$ |
|---|---|---|---|
| 1 | 1.67 | 88.05 | 11 |
| 2 | 9.2 | 82.65 | 11 |
| 3 | 0.83 | 89.4 | 7 |
| 4 | 0.41 | 94.8 | 11 |
| 5 | 1.67 | 89.4 | 9 |
| 6 | 0.83 | 96.1 | 59 |
| 7 | 10.04 | 92.1 | 9 |

The method disclosed herein in addition to authentication, enables constantly validating the authenticated session. This can prevent potential misuse of the device/system by another user post authentication. Constant re-authentication, however, can be annoying, particularly on a wearable device with limited screen real estate and or limited input mechanisms. Thus, the method disclosed herein utilizes PPG sensor data to maintain an authentication session and results in low false negative rate—which essentially translates to fewer reauthentication requests to the user.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means, and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method for continuously validating a user during an established authenticated session, the method comprising steps of:
   detecting, by one or more hardware processors, the established authenticated session of a user, wherein the user is authenticated during a session establishment process using an authentication mechanism;
   simultaneously receiving, by the one or more hardware processors, a Photoplethysmogram (PPG) signal from a PPG sensor of a wearable device worn by the authenticated user;
   preprocessing, by the one or more hardware processors, the PPG signal to determine a set of PPG segments with minimal motion artifact presence, wherein each of the set of PPG segments is greater than a preset window size, and wherein the preprocessing selects portions of the received PPG signal corresponding to portions of an synchronized accelerometer data received from an accelerometer sensor of the wearable device, and the selected portions of the synchronized accelerometer data indicate minimal motion artifacts based on a preset motion artifact threshold;
   selecting, by the one or more hardware processors:
      a first PPG segment among the set of PPG segments as a reference segment, post detection of the established authenticated session, and
      a succeeding segment to the first segment as a test segment;
   determining, by the one or more hardware processors, a number of PPG pulses (I), with pulse ($p_i$), where $i \in 1, 2, \ldots, I-1$) present in the test segment and a number of PPG pulses (J) with pulse ($p_j$), where $j \in 1, 2, \ldots, J-1$) present in the reference segment by applying trough to trough detection;
   stretching in time and normalizing in area, by the one or more hardware processors, each pulse ($p_j$) among the number of PPG pulses (I) and each pulse ($p_i$) among the number of PPG pulses (J);
   performing, by the one or more hardware processors, a template matching between the stretched PPG pulses (I) of the test segment and the stretched PPG pulses (J) of the reference segment by:
      computing a minimum distance vector $d_{test}[i]$, of pulse $p_i$ for all $i \in 1, 2, \ldots, I-1$, by comparing with each of the number of PPG pulses (J) using a Euclidean distance similarity measure; and
      computing a minimum distance vector $d_{ref}[j]$, of pulse $p_j$ for all $j \in 1, 2, \ldots, J-1$ by comparing with each of the number of PPG pulses (I) using the Euclidean distance similarity measure, when $j \neq i$;
   computing, by the one or more hardware processors, distributions for all $d_{test}[i]$ and $d_{ref}[j]$; and
   validating, by the one or more hardware processors, the user participating in the established authenticated session if a validation criterion is satisfied, wherein the validation criterion maps the test segment to the reference segment if percentage of distances in $d_{test}$, for $d_{test}$>a distance criterial ($d_1$), is less than a percentage based threshold ($t_2$).

2. The method as claimed in claim 1, further comprising reselecting the test segment as the reference segment if the validation criterion is satisfied; and repeating the steps of continuously validating the user during the established authenticated session.

3. The method as claimed in claim 1, further comprising:
   invalidating the user corresponding to the test segment if the validation criterion is dissatisfied;
   closing the established authenticated session;
   requesting the user to reauthenticate using the authentication mechanism to re-establish an authenticated session; and
   repeating the steps of continuously validating the user during the re-established authenticated session based on a reference segment and a test segment identified for the re-established authenticated session.

4. The method as claimed in claim 1, wherein the stretching is performed to a predefined time width of 625 milliseconds with 40 samples at a sampling rate of 64 Hz.

5. The method as claimed in claim 1, wherein a value of the distance criterial ($d_1$) is derived from a percentile based threshold ($t_1$) such that ($t_1$) percentile of the distance vector $d_{ref}$ is below the distance criterial ($d_1$).

6. A system for continuously validating an authenticated user during an established authenticated session, the system comprising: a memory storing instructions; one or more Input/Output (I/O) interfaces; and one or more hardware processors coupled to the memory via the one or more I/O interfaces, wherein the one or more hardware processors are configured by the instructions to: detect the established authenticated session of a user, wherein the user is authenticated during a session establishment process using an authentication mechanism; simultaneously receive a Photoplethysmogram (PPG) signal from a PPG sensor of a wearable device worn by the authenticated user; preprocess the PPG signal to determine a set of PPG segments with minimal motion artifact presence, wherein each of the set of PPG segments is greater than a preset window size, and wherein the preprocessing selects portions of the received PPG signal corresponding to portions of an synchronized accelerometer data received from an accelerometer sensor of the wearable device, and the selected portions of the synchronized accelerometer data indicate minimal motion artifacts based on a preset motion artifact threshold; select: a first PPG segment among the set of PPG segments as a reference segment, post detection of the established authenticated session, and a succeeding segment to the first segment as a test segment; determine a number of PPG pulses (I), with pulse (pi), where i E 1, 2, . . . , I−1) present in the test segment and a number of PPG pulses (J) with pulse (pj), where j E 1, 2, . . . , J−1) present in the reference segment by applying trough to trough detection; stretch in time and normalize in area each pulse (pi) among the number of PPG pulses (I) and each pulse (pj) among the number of PPG pulses (J); perform a template matching between the stretched PPG pulses (I) of the test segment and the stretched PPG pulses (J) of the reference segment by: computing a minimum distance vector $d_{test}$ [i], of pulse pi for all i E 1, 2, . . . , I−1, by comparing with each of the PPG pulses (J) using a Euclidean distance similarity measure; and computing a minimum distance vector $d_{ref}$[j], of pulse pj for all j E 1, 2, . . . , J−1 by comparing with each of the number of PPG pulses (I) using the Euclidean distance similarity measure, when j≠i; compute distributions for all $d_{test}$ [i] and $d_{ref}$ [j]; and validate the user participating in the established authenticated session if a validation criterion is satisfied, wherein the validation criterion maps the test segment to the reference segment if percentage of distances in $d_{test}$, for $d_{test}$>a distance criterial ($d_1$), is less than a percentage threshold ($t_2$).

7. The system as claimed in claim 6, wherein the one or more hardware processors are further to reselect the test segment as the reference segment if the validation criterion is satisfied and repeat the steps of continuously validating the user during the established authenticated session.

8. The system as claimed in claim 6, wherein the one or more hardware processors are further configured to:
invalidate the user corresponding to the test segment if the validation criterion is dissatisfied;
close the established authenticated session;
request the user to reauthenticate using the authentication mechanism to re-establish an authenticated session; and
repeat the steps of continuously validating the user during the re-established authenticated session based on a reference segment and a test segment identified for the re-established authenticated session.

9. The system as claimed in 6, wherein the one or more hardware processors are configured to stretch each pulse to a predefined time width of 625 milliseconds with 40 samples at a sampling rate of 64 Hz.

10. The system as claimed in claim 6, wherein the one or more hardware processors are configured to derive a value of the distance criterial ($d_1$) a percentile based threshold ($t_1$) such that ($t_1$) percentile of the distance vector $d_{ref}$ is below the distance criterial ($d_1$).

11. One or more non-transitory machine readable information storage mediums comprising one or more instructions, which when executed by one or more hardware processors causes a method for continuously validating an authenticated user during an established authenticated session using Photoplethysmogram (PPG) and accelerometer data, the method comprising:
detecting the established authenticated session of a user, wherein the user is authenticated during a session establishment process using an authentication mechanism;
simultaneously receiving a Photoplethysmogram (PPG) signal from a PPG sensor of a wearable device worn by the authenticated user;
preprocessing the PPG signal to determine a set of PPG segments with minimal motion artifact presence, wherein each of the set of PPG segments is greater than a preset window size, and wherein the preprocessing selects portions of the received PPG signal corresponding to portions of an synchronized accelerometer data received from an accelerometer sensor of the wearable device, and the selected portions of the synchronized accelerometer data indicate minimal motion artifacts based on a preset motion artifact threshold;
selecting:
a first PPG segment among the set of PPG segments as a reference segment, post detection of the established authenticated session, and
a succeeding segment to the first segment as a test segment;
determining a number of PPG pulses (I), with pulse ($p_{i,}$), where i∈1, 2, . . . , I−1) present in the test segment and a number of PPG pulses (J) with pulse ($p_j$), where j∈1, 2, . . . , J−1) present in the reference segment by applying trough to trough detection;
stretching in time and normalizing in area each pulse ($p_{j,}$) among the number of PPG pulses (I) and each pulse ($p_i$) among the number of PPG pulses (J);
performing a template matching between the stretched PPG pulses (I) of the test segment and the stretched PPG pulses (J) of the reference segment by:
computing a minimum distance vector $d_{test}$ [i], of pulse $p_i$ for all i∈1, 2, . . . , I−1, by comparing with each of the number of PPG pulses (J) using a Euclidean distance similarity measure; and
computing a minimum distance vector $d_{ref}$ [j], of pulse $p_j$ for all j∈1, 2, . . . , J−1 by comparing with each of the number of PPG pulses (I) using the Euclidean distance similarity measure, when j≠i;
computing, (216), by the one or more hardware processors, distributions for all $d_{test}$ [i] and $d_{ref}$ [j]; and validating the user participating in the established authenticated session if a validation criterion is satisfied, wherein the validation criterion maps the test segment to the reference segment if percentage of distances in $d_{test}$, for $d_{test}>$a distance criterial $(d_1)$, is less than a percentage based threshold $(t_2)$.

12. The one or more non-transitory machine readable information storage mediums of claim 11, further comprising reselecting the test segment as the reference segment if the validation criterion is satisfied; and repeating the steps of continuously validating the user during the established authenticated session.

13. The one or more non-transitory machine readable information storage mediums of claim 11, further comprising:
   invalidating the user corresponding to the test segment if the validation criterion is dissatisfied;
   closing the established authenticated session;
   requesting the user to reauthenticate using the authentication mechanism to re-establish an authenticated session; and
   repeating the steps of continuously validating the user during the re-established authenticated session based on a reference segment and a test segment identified for the re-established authenticated session.

14. The one or more non-transitory machine readable information storage mediums of claim 11, wherein the stretching is performed to a predefined time width of 625 milliseconds with 40 samples at a sampling rate of 64 Hz.

15. The one or more non-transitory machine readable information storage mediums of claim 11, wherein a value of the distance criterial $(d_1)$ is derived from a percentile based threshold $(t_1)$ such that $(t_1)$ percentile of the distance vector $d_{ref}$ is below the distance criterial $(d_1)$.

* * * * *